United States Patent
Milne et al.

(10) Patent No.: US 12,226,777 B2
(45) Date of Patent: Feb. 18, 2025

(54) APPARATUS FOR RESOLVING IMAGING PROBLEMS CAUSED BY THE MENISCUS

(71) Applicant: AMGEN INC., Thousand Oaks, CA (US)

(72) Inventors: Graham F. Milne, Ventura, CA (US); Tony Y. Wang, League City, TX (US)

(73) Assignee: AMGEN INC., Thousand Oaks, CA (US)

( * ) Notice: Subject to any disclaimer, the term of this patent is extended or adjusted under 35 U.S.C. 154(b) by 846 days.

(21) Appl. No.: 17/415,442

(22) PCT Filed: Dec. 16, 2019

(86) PCT No.: PCT/US2019/066454
§ 371 (c)(1),
(2) Date: Jun. 17, 2021

(87) PCT Pub. No.: WO2020/131662
PCT Pub. Date: Jun. 25, 2020

(65) Prior Publication Data
US 2022/0040689 A1    Feb. 10, 2022

Related U.S. Application Data

(60) Provisional application No. 62/781,797, filed on Dec. 19, 2018.

(51) Int. Cl.
*B01L 3/00* (2006.01)
*B01F 23/00* (2022.01)
(Continued)

(52) U.S. Cl.
CPC ........... *B01L 3/50853* (2013.01); *B01L 9/523* (2013.01); *G01N 21/17* (2013.01);
(Continued)

(58) Field of Classification Search
CPC ............... B01L 3/50853; B01L 9/523; B01L 2300/046; B01L 2300/0829; G01N 21/17;
(Continued)

(56) References Cited

U.S. PATENT DOCUMENTS 6,074,614 A    6/2000   Hafeman et al.
2017/0067006 A1    3/2017   Obi et al.

FOREIGN PATENT DOCUMENTS

CN    101163551 A    4/2008
JP    2010190796 A    9/2010
(Continued)

OTHER PUBLICATIONS

Japanese Patent Application No. 2021-534713, Office Action, mailed Oct. 10, 2023.
(Continued)

*Primary Examiner* — Jennifer Wecker
*Assistant Examiner* — Oyeleye Alexander Alabi
(74) *Attorney, Agent, or Firm* — MARSHALL, GERSTEIN & BORUN LLP (57) ABSTRACT

A well plate cover includes a base defining a base plane, and a plurality of insertion elements. At least a portion of each of the insertion elements is transparent. Each of the insertion elements is coupled to the base, and extends, in a direction orthogonal to the base plane, from the base to a distal end surface of the insertion element. The distal end surface of each of the insertion elements includes an apex that, when the respective insertion element is inserted into a well of a well plate, extends further into the well than any other portion of the distal end surface. The apex is a point, a line, or a plane having a diameter that is less than one half of a maximum diameter of the distal end surface.

4 Claims, 7 Drawing Sheets

(51) Int. Cl.

| | |
|---|---|
| *B01F 23/41* | (2022.01) |
| *B01F 101/23* | (2022.01) |
| *B01L 9/00* | (2006.01) |
| *B23Q 17/24* | (2006.01) |
| *C07K 14/705* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 21/17* | (2006.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 21/77* | (2006.01) |
| *G01N 21/78* | (2006.01) |
| *G01N 27/414* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *G01N 35/00* | (2006.01) |
| *G01N 35/10* | (2006.01) |
| *G06T 7/00* | (2017.01) |
| *G06T 7/90* | (2017.01) |
| *H10K 10/46* | (2023.01) |
| *H10K 85/00* | (2023.01) |
| *H10K 85/20* | (2023.01) |

(52) U.S. Cl.
CPC . *B01L 2300/046* (2013.01); *B01L 2300/0829* (2013.01); *G01N 2021/1765* (2013.01); *G01N 2201/0639* (2013.01)

(58) Field of Classification Search
CPC ... G01N 2021/1765; G01N 2201/0639; C12M 23/12; C12M 23/22; C12M 23/38; G02B 21/34

See application file for complete search history.

(56) References Cited

FOREIGN PATENT DOCUMENTS

| WO | WO-02087763 A1 * | 11/2002 | .......... B01L 3/50853 |
|---|---|---|---|
| WO | WO-2010/105845 A2 | 9/2010 | |
| WO | WO-2010/105845 A3 | 1/2011 | |
| WO | WO-2016/120757 A1 | 8/2016 | |

OTHER PUBLICATIONS

Search Report and Written Opinion in International Application No. PCT/US2019/066454 dated Mar. 25, 2020, 12 pages.

Hartmann et al., "Eppendorf Cell Culture Consumables—Improved Optical Performance Facilitates Microscopic Analysis of Cells", Eppendorf, Application Note No. 330, Jun. 2014, 8 pages.

Trevor DeVaney, "Plate Imaging Inserts for Meniscus Correction", Medical University of Graz, Technology Offer, Jun. 2008, 1 page.

* cited by examiner

APPARATUS FOR RESOLVING IMAGING PROBLEMS CAUSED BY THE MENISCUS

CROSS-REFERENCE TO RELATED APPLICATION

Priority is claimed to U.S. Provisional Patent Application No. 62/781,797, filed Dec. 19, 2018, the entire contents of which are hereby incorporated herein by reference.

FIELD OF DISCLOSURE

The present application relates to techniques for imaging wells or other vessels containing fluid samples.

BACKGROUND

In certain contexts, such as cell line monitoring or quality control procedures for manufactured drug products, it is necessary to examine fluid samples. For example, it may be necessary to identify and/or characterize particles (e.g., cells, debris, etc.) in a fluid. A common way of inspecting such samples is to inject the samples into wells of a well plate, after which an automated system shifts the well plate such that each of the wells is sequentially aligned with the optical path of an imager. As each well is aligned with the optical path, the imager captures one or more images of the well. The well images may then be stored and analyzed by a human analyst, and/or by a computer.

Figure 1A:
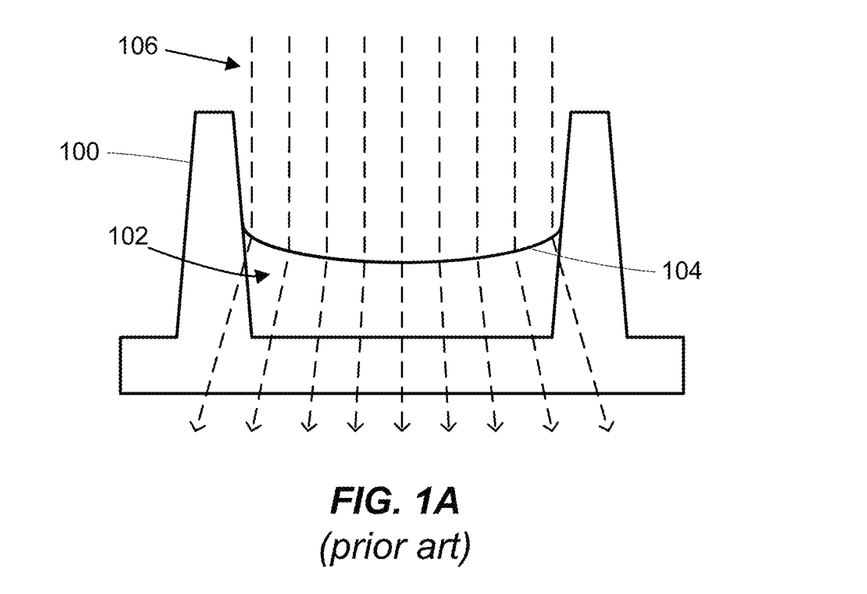
FIGS. 1A-1D are cross-sectional diagrams depicting various conventional well imaging techniques.

To ensure a robust inspection, the well images must maintain a certain level of quality (e.g., resolution, focus, etc.). However, various factors can make this challenging, such as well wall shadows and limitations on the resolution of the imager. One cause of sub-optimal images is the meniscus (upper curved surface) that forms due to the intermolecular attraction between the fluid and the well walls. Due to the small diameter of the typical well, the meniscus can significantly distort the well image. FIG. 1A provides an illustration, with a well 100 containing a fluid sample 102 that forms a meniscus 104. Well 100 typically has a transparent bottom, allowing incident light 106 from an illumination source to pass through both fluid sample 102 and well 100, after which an imager (e.g., a charge-coupled device (CCD) camera) captures an image of fluid sample 102. As seen in FIG. 1A, the curvature of meniscus 104 causes incident light 106 to refract at an angle that increases with proximity to the wall of well 100. This refraction degrades the phase contrast, which in turns reduces the image quality.

Figure 1B:
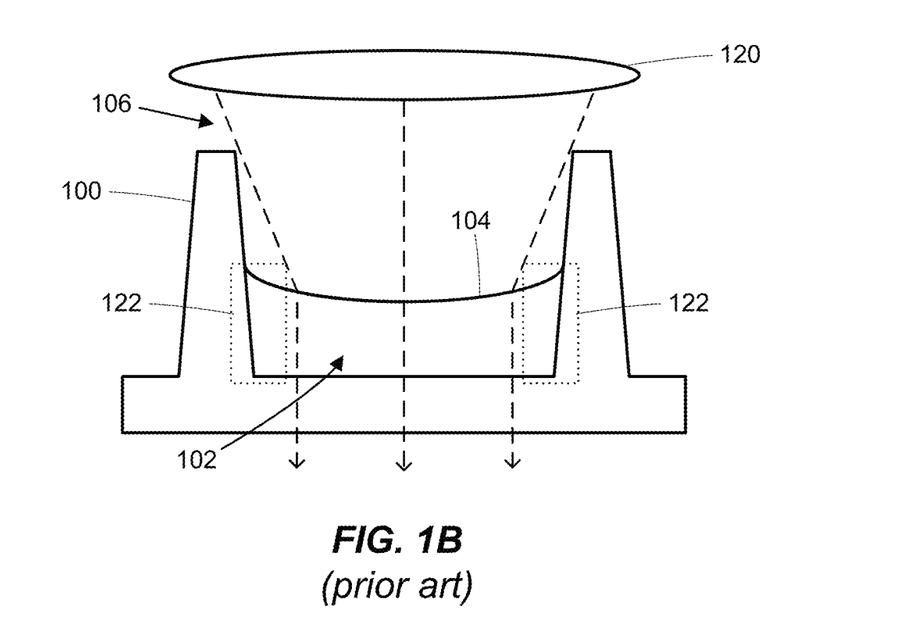
Figure 1C:
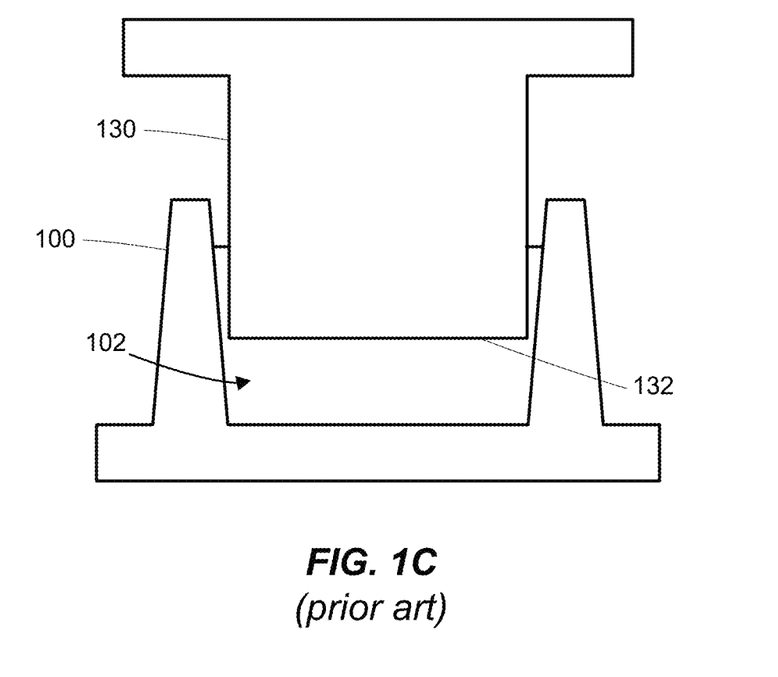
Figure 1D:
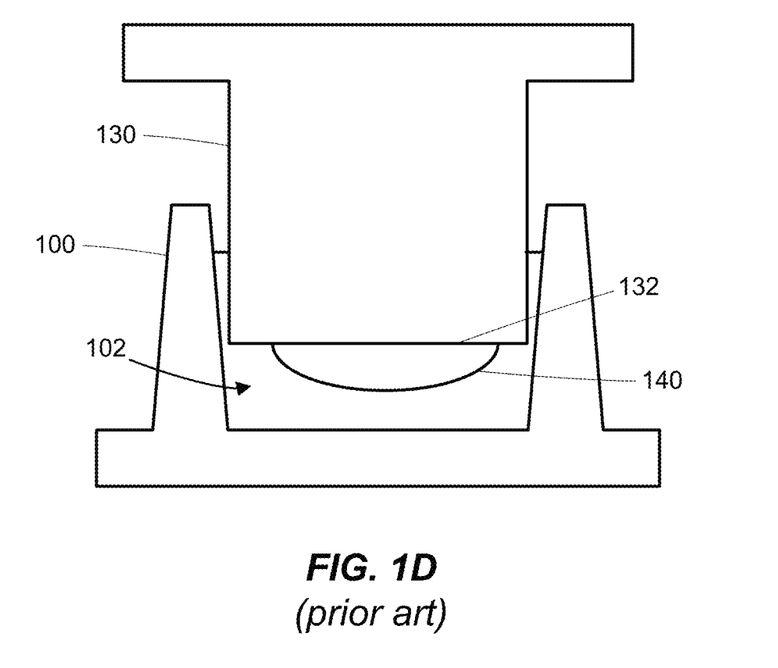

Several techniques for resolving the problems created by the meniscus have been proposed. For example, an imaging system may compensate for the meniscus refraction by using a lens that distributes light on the sample in a non-uniform manner. One such example is shown in FIG. 1B, where a lens 120 is used to compensate for the refraction of incident light 106 by meniscus 104. As seen in FIG. 1B, however, this technique can result in a failure to image an annular portion 122 of well 100 near the perimeter. Annular portion 122 can be large enough that, in some applications, the failure to image portion 122 is unacceptable. An alternative proposal is shown in FIG. 1C, where an element 130 (e.g., of a well plate "cover") with a flat surface 132 is inserted into well 100 and fluid sample 102. As seen in FIG. 1D, however, this may result in an air bubble 140 being trapped between flat surface 132 and fluid sample 102. Air bubbles of this sort can distort the well image in a manner for which it is very difficult to compensate, e.g., due to the variable position, size and shape of bubbles. While some rounding of the edges of the flat surface has been suggested, the large flat area still allows bubbles to be trapped in a significant number of samples. Thus, there is a need for an apparatus or technique that resolves the imaging problems created by the meniscus, while still permitting imaging of substantially the entire well, and without introducing (or at least, making less likely) air bubbles that may distort the well image.

SUMMARY

Embodiments described herein relate to systems and methods that improve upon conventional techniques for imaging fluid-filled vessels by resolving certain problems relating to the fluid meniscus. For a given vessel, an insertion element is inserted into the fluid within the vessel. The insertion element may be wholly transparent, or may only be transparent in certain areas. The vessel may be a well within a well plate (e.g., a 96-well microplate), and the insertion element may be one of multiple insertion elements protruding from the base of a well plate cover, for example. When entering the fluid, the insertion element disrupts the meniscus. Imaging may then occur by illuminating the fluid/vessel from the top side (through the insertion element), and using an imager (e.g., a charge-coupled device (CCD) camera) to capture light that travels through a transparent bottom side of the vessel (e.g., after refracting off of particles or other contents of the fluid), for example.

To reduce the likelihood that the insertion process results in air bubbles being trapped between the insertion element and the fluid, the distal end surface of the insertion element (i.e., the surface that faces the fluid just prior to insertion, and becomes at least partially submerged after insertion) is designed/configured in a particular manner. Specifically, the distal end surface includes an apex that first comes into contact with the fluid as the insertion element is inserted, and the rest of the distal end surface recedes from the apex in a step-wise or continuous manner when progressing, in any direction, from the apex out towards the perimeter of the insertion element.

The apex may be a single point or a line. Alternatively, the apex may be a plane having a diameter that is less than one half of the maximum diameter of the distal end surface (when viewed from the direction of insertion). Thus, the insertion element may take any one of many possible forms. For instance, the insertion element may be, or may include, a cone, a cylindrical step pyramid, a wedge, a frustum, and so on. Moreover, the apex may or may not be aligned with a center of the distal end surface, and thus may or may not form a symmetrical shape. For example, the insertion element may include a symmetrical cone with an apex point at the center of the distal end surface, or the distal end surface may be entirely sloped in one direction (i.e., if the apex is a point along the perimeter of the distal end surface). In some embodiments, the insertion element may include a cylindrical or other-shaped element at or near its proximal end, in order to space the distal end surface of the insertion element further away from the base of a well plate cover. Alternatively, the base itself may include additional spacing components that perform this function, or no such spacing elements may be needed.

By initially contacting the fluid with only a relatively small area, and by monotonically receding away from the apex in any direction from the apex out towards the perimeter, the insertion element is less likely to trap air bubbles as the element is inserted into the vessel. Thus, the image distortion caused by the meniscus is substantially removed without introducing (or at least, while lowering the likelihood of introducing) air bubbles as a new source of image distortion.

BRIEF DESCRIPTION OF THE DRAWINGS

The skilled artisan will understand that the figures, described herein, are included for purposes of illustration and do not limit the present disclosure. The drawings are not necessarily to scale, and emphasis is instead placed upon illustrating the principles of the present disclosure. It is to be understood that, in some instances, various aspects of the described implementations may be shown exaggerated or enlarged to facilitate an understanding of the described implementations. In the drawings, like reference characters throughout the various drawings generally refer to functionally similar and/or structurally similar components.

DETAILED DESCRIPTION

The various concepts introduced above and discussed in greater detail below may be implemented in any of numerous ways, and the described concepts are not limited to any particular manner of implementation. Examples of implementations are provided for illustrative purposes.

Figure 2:
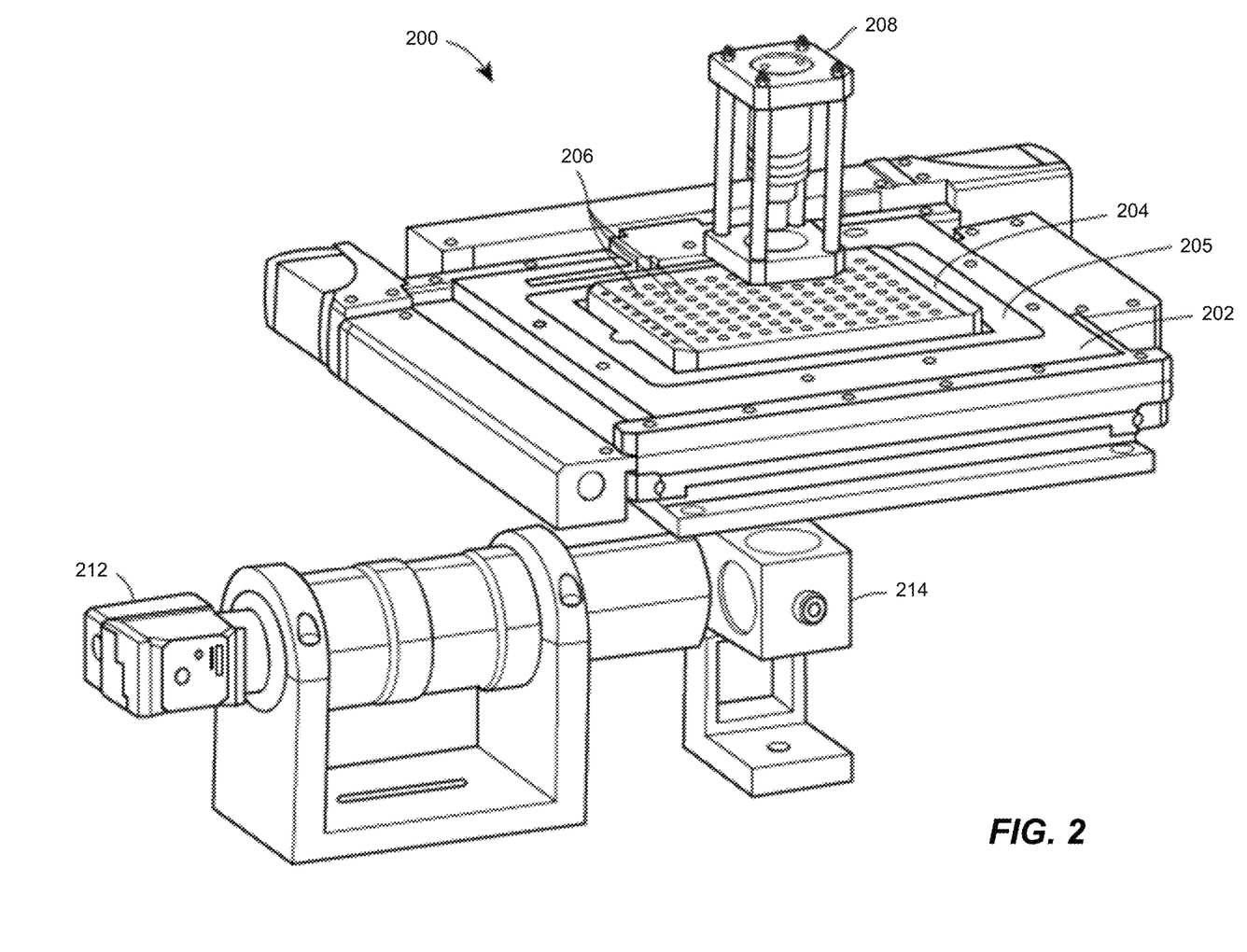
FIG. 2 depicts an example visual inspection system that may be used with any of the well plate covers described herein.

FIG. 2 depicts an example visual inspection system 200 that may be used with any of the well plate covers described below in connection with FIGS. 3 through 6. As seen in FIG. 2, visual inspection system 200 includes a stage 202 that is configured to receive a well plate 204 containing a number of wells 206. In some embodiments, stage 202 includes a plate holder 205 that functions as an adaptor between stage 202 and well plate 204 to facilitate receipt of well plate 204 for imaging of individual wells 206. In some embodiments, stage 202 is configured to accept multiple plate holders having varying sizes and/or shapes. For example, stage 202 may include several nested, adjustable, and/or interchangeable cavities or other formed parts that accept different types of plate holders. Well plate 204 may be a microplate including any suitable number of wells 206 disposed thereon (e.g., 6, 24, 96, 384, 1536, etc.). Wells 206 may be arranged in any suitable pattern on well plate 204, such as a 2:3 rectangular matrix, for example. Each well 206 holds a volume of fluid that may be in the range of tens of nanoliters up to several milliliters, for example. As a more specific example, well plate 204 may be a 96-well microplate, with each well 206 being capable of holding up to 200 microliters of fluid.

Visual inspection system 200 further includes an illumination system 208, an imager 212 (e.g., a charge-coupled device (CCD) camera) that is configured to acquire images and, in some embodiments, an optical system 214 that directs light to imager 212. Illumination system 208 may include any suitable number and/or type(s) of light source(s) configured to generate source light, and illuminates each well 206 when that well is positioned in the optical path of imager 212. In various embodiments, each of wells 206 may have one or more transparent and/or opaque portions. For example, each of wells 206 may be entirely transparent, or may have transparent bottoms with the side walls being opaque. If present in visual inspection system 200, optical system 214 may include one or more mirrors and/or other optical elements designed to redirect the source light to imager 212 (e.g., including source light that has refracted off of the contents of one of wells 206 and/or the well itself).

Visual inspection system 200 images each of wells 206 sequentially. To this end, visual inspection system 200 is configured to move stage 202 along one or more (e.g., x and y) axes to successively align each of wells 206 with the illumination system 208 and the optical path of imager 212 for individual well analysis. For example, stage 202 may be coupled to one or more motorized actuators. As each of wells 206 is aligned with illumination system 208 and the optical path of imager 212, imager 212 acquires one or more images of the illuminated well.

It is understood that FIG. 2 shows only one example embodiment of visual inspection system 200, and that others are possible. For example, visual inspection system 200 may include multiple imagers similar to imager 212, or may omit optical system 214, etc. As another example, wells 206 may not be imaged sequentially, one at a time and each in its entirety. For example, visual inspection system 200 may instead include wider field-of-view optics to image multiple wells 206 at once. Conversely, visual inspection system 200 may include higher-magnification optics to capture only a portion of a single well 206 in a single image, with multiple images being stitched together to form a composite image of the well 206. Moreover, while not shown in FIG. 2, visual inspection system 200 may include one or more processors to provide local control of the operations of stage 202, illumination system 208, and imager 212 (e.g., in response to commands received from another computer system).

Figure 3A:
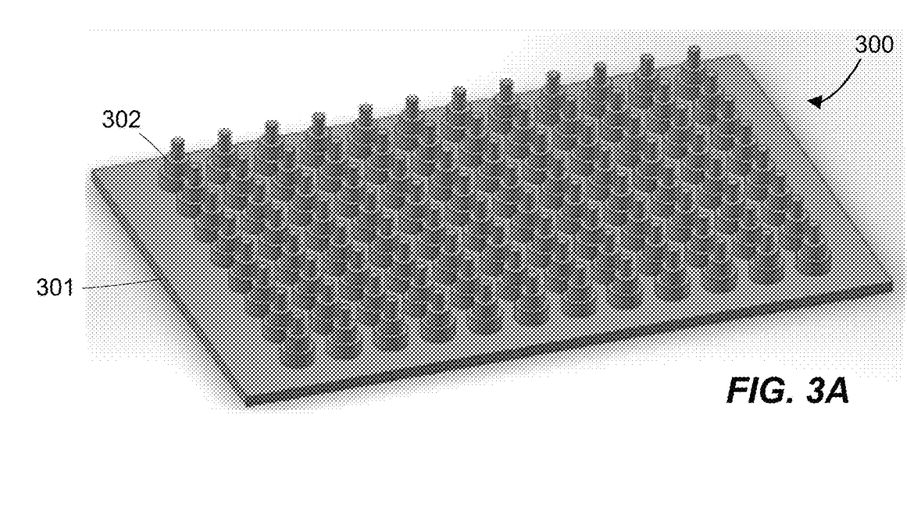
FIGS. 3A-3C depict a first embodiment of a well plate cover that may be used to resolve problems associated with the imaging of fluid samples in wells.
Figure 3B:
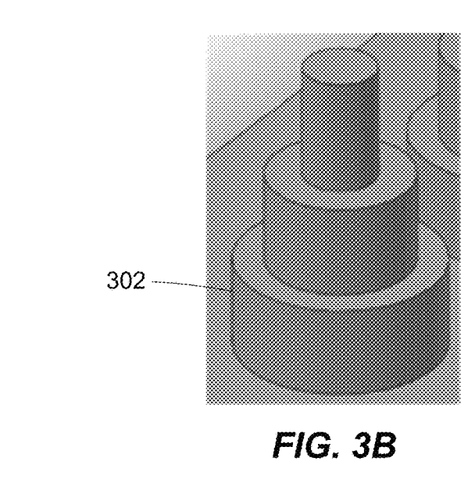
Figure 3C:
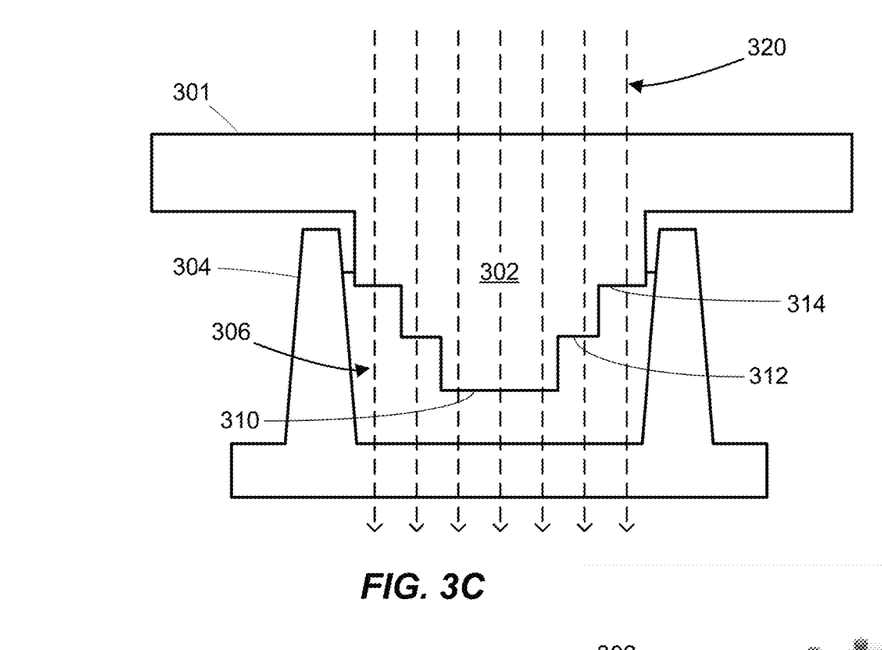

FIGS. 3A-3C depict a well plate cover 300 that may be used to resolve problems associated with the imaging of fluid samples in wells. Well plate cover 300 may be used as a cover that fits to well plate 204, when imaging wells 206 with visual inspection system 200 of FIG. 2 as described above, for example. Referring first to FIG. 3A, well plate cover 300 includes a planar base 301, from which protrude a number of insertion elements 302. In some embodiments, well plate cover 300 is a single, monolithic component. For example, the entire well plate cover 300 may be made of polystyrene, polypropylene, glass, or any other suitable transparent material. In other embodiments, insertion elements 302 are at least in part formed separately from (and/or of a different material than) base 301, with base 301 being either opaque, translucent or transparent. In the example shown in FIG. 3A, well plate cover 300 provides 96 insertion elements 302 for a standard 96-well microplate. In other embodiments, however, well plate cover 300 may include more or fewer insertion elements 302, and/or may arrange insertion elements 302 in a different pattern on base 301. In still other embodiments, insertion elements 302 are not coupled to any base, and are inserted into wells (or other vessels) individually.

FIG. 3B provides a closer, 3D-perspective view of one of insertion elements 302, and FIG. 3C provides a cross-sectional view (not drawn to scale) of one of insertion elements 302. As the term is used herein, a "distal end surface" of an insertion element is the (possibly multi-faceted) surface of the insertion element that at least partially comes into contact with a fluid when the insertion element is properly inserted into a fluid-filled vessel (e.g., well). Thus, as seen in FIGS. 3B and 3C, each insertion element 302 has a distal end surface having/defining a cylindrical, stepped pyramid shape.

Referring specifically now to FIG. 3C, when insertion element 302 is being inserted into a well 304 containing a fluid 306 (e.g., into one of wells 206 of FIG. 2), an apex plane 310 of insertion element 302 first contacts fluid 306. As insertion element 302 is inserted further into well 304, a first concentric tier 312 and then a second concentric tier 314 successively come into contact with fluid 306. Tier 314 is larger than tier 312, and may be sized such that tier 314 can extend into well 304 at least some desired distance without allowing too much of fluid 306 to escape up and around the perimeter of insertion element 302, and/or without allowing fluid 306 to form an appreciable meniscus outside the perimeter of insertion element 302. If well 304 has a base diameter of 6.35 mm and a top diameter of 6.86 mm, for example, tier 314 may have a diameter between 6.4 mm and 6.5 mm (to leave a small gap for air to escape). The depth of insertion element 302 (i.e., as measured from its proximal end where insertion element 302 joins base 301, to apex plane 310) may provide enough sloping to allow air bubbles to quickly escape to the atmosphere, without causing apex plane 310 to contact the bottom of well 304 and without displacing too much of fluid 306. For example, apex plane 310 may protrude from base 301 by 6 mm (e.g., with tier 314 being spaced 2 mm from base 301, tier 312 being spaced 2 mm from tier 314, and apex plane 310 being spaced 2 mm from tier 312, or with an uneven spacing of tiers). The appropriate thickness for each tier of insertion element 302 may depend on the fluid fill volume. For lower fill volumes, for example, insertion element 302 may need to protrude further from base 301 to ensure that insertion element 302 fully engages/interacts with the fluid.

In conjunction with the diameter of tier 314, the diameters of apex plane 310 and tier 312 may be set such that there is no flat area, parallel to base 301, that is sufficiently large to allow an air (or other gas) bubble to reside in a steady state condition (e.g., given the range of bubble sizes that are typical for a particular well size, and/or a particular type of fluid sample, etc.). In some embodiments, for example, apex plane 310 and tier 312 may be designed such that the diameter of apex plane 310, the width of shelf formed by tier 312, and the width of the shelf formed by tier 314 are all substantially less than an expected bubble diameter.

Once insertion element 302 is fully inserted (e.g., with base 301 being some desired distance away from well 304, or in contact with well 304), fluid 306 may be imaged. Light 320 (e.g., sourced by illumination system 208 of FIG. 2) passes through the transparent insertion element 302 (or the transparent portion thereof) and, due to the lack of an appreciable meniscus and the planar structure of insertion element 302 (i.e., with tiers 312, 314 and apex plane 310 that are all parallel to base 301 and the bottom of well 304), there is relatively little refraction other than that which is caused by the contents of fluid 306 (i.e., the refraction needed to produce an accurate image of the fluid contents) and possibly portions of well 304. As seen in FIG. 3C, there may be a modest amount of fluid 306 that extends outside and above tier 314 when insertion element 302 is fully inserted. In some embodiments where base 301 is also transparent, however, the entire well 304 and all of fluid 306 can nevertheless be imaged with insertion element 302 inserted. In particular, base 301 may function as a third concentric tier similar to tiers 312 and 314, allowing light to pass around the perimeter of insertion element 302 without significantly refracting the light.

Figure 4A:
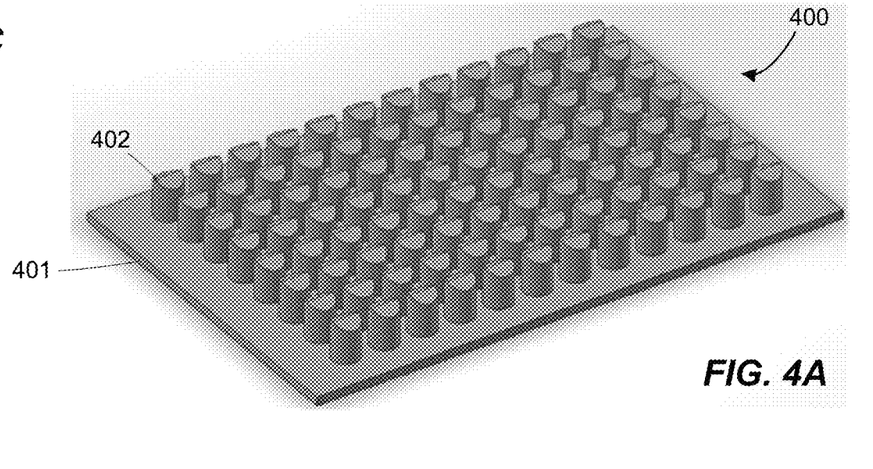
FIGS. 4A-4C depict a second embodiment of a well plate cover that may be used to resolve problems associated with the imaging of fluid samples in wells.
Figure 4B:
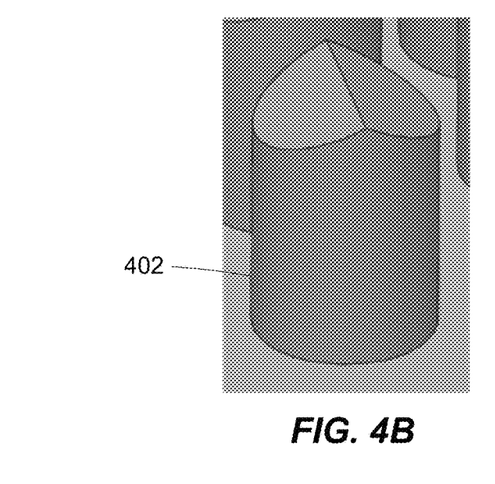
Figure 4C:
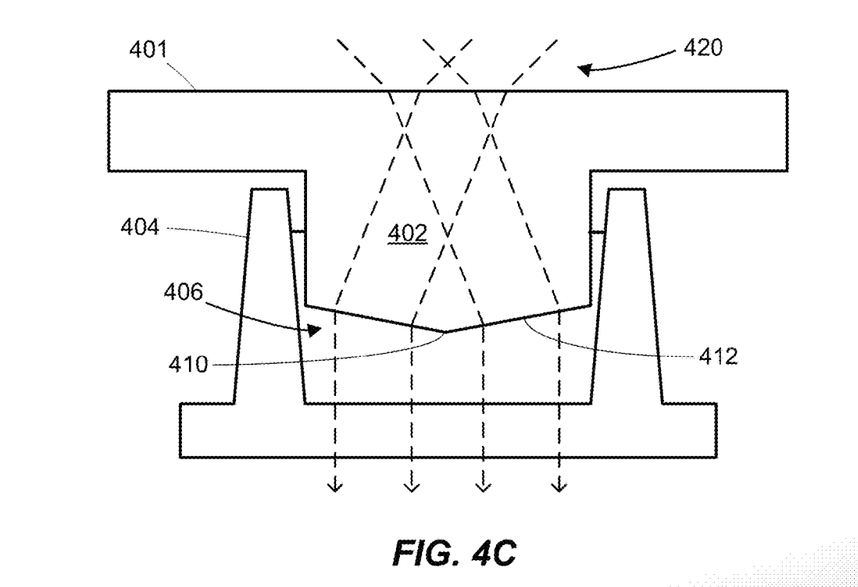

FIGS. 4A-4C depict an alternative well plate cover 400 that may be used to resolve problems associated with the imaging of fluid samples in wells. Like well plate cover 300, well plate cover 400 may be used as a cover that fits to well plate 204, when imaging wells 206 with visual inspection system 200 of FIG. 2 as described above. Referring first to FIG. 4A, well plate cover 400 includes a planar base 401, from which protrude a number of insertion elements 402. In some embodiments, well plate cover 400 is a single, monolithic component. For example, the entire well plate cover 400 may be made of polystyrene, polypropylene, glass, or any other suitable transparent material. In other embodiments, insertion elements 402 are at least in part formed separately from (and/or of a different material than) base 401. In the example shown in FIG. 4A, well plate cover 400 provides 96 insertion elements 402 for a standard 96-well microplate. In other embodiments, however, well plate cover 400 may include more or fewer insertion elements 402, and/or may arrange insertion elements 402 in a different pattern on base 401. In still other embodiments, insertion elements 402 are not coupled to any base, and are inserted into wells (or other vessels) individually.

FIG. 4B provides a closer, 3D-perspective view of one of insertion elements 402, and FIG. 4C provides a cross-sectional view (not drawn to scale) of one of insertion elements 402. As seen in FIGS. 4B and 4C, each insertion element 402 has a distal end surface having/defining a cylindrical wedge shape. Referring specifically now to FIG. 4C, when insertion element 402 is being inserted into a well 404 containing a fluid 406 (e.g., into one of wells 206 of FIG. 2), an apex line 410 of insertion element 402 first contacts fluid 406. As insertion element 402 is inserted further into well 404, a sloped portion 412, which recedes from the apex line in opposite directions, then comes into contact with fluid 406. Insertion element 402 may be sized such that its maximum-diameter (cylindrical) portion can fit into well 404 with some tolerance, without allowing fluid 406 to form an appreciable meniscus outside the perimeter of insertion element 402. If well 404 has a base diameter of 6.35 mm and a top diameter of 6.86 mm, for example, insertion element 402 may have a diameter between 6.4 mm and 6.5 mm (to leave a small gap for air to escape). The total length of insertion element 402 may be set such that, when insertion element 402 is fully inserted into well 404, apex line 410 does not contact the bottom of well 404, but some, most or all of sloped portion 412 is submerged. For example, apex line 410 may be 6 mm away from base 401, in a direction orthogonal to base 401. The slope of sloped portion 412 may be such that air (or other gas) bubbles can quickly escape to the atmosphere. For example, sloped portion 412 may protrude 1 mm further into well 404 for every 3 mm traveled in a direction from the perimeter of insertion element 402 towards the center point of apex line 410 (or 0.5 mm further for every 3 mm, etc.). The appropriate length of insertion element 402 (i.e., the spacing between apex line 410 and base 401) may depend on the fluid fill volume. For lower fill volumes, for example, insertion element 402 may need to protrude further from base 401 to ensure that insertion element 402 fully engages/interacts with the fluid. While FIGS. 4A-4C depict an embodiment in which apex line 410 evenly divides two halves of sloped portion 412, in other embodiments apex line 410 does not pass through the center of insertion element 402, and/or apex line 410 is not a straight line.

Once insertion element 402 is fully inserted (e.g., with base 401 being some desired distance away from well 404, or in contact with well 404), fluid 406 may be imaged, with light 420 (e.g., sourced by illumination system 208 of FIG. 2) to provide illumination. However, to compensate for light refraction caused by sloped portion 412, light 420 may be provided at an angle (rather than orthogonal to base 401), as seen in FIG. 4C. If a collimated light source is used, for example, light 420 may be provided at the desired angle by inserting a prism between the light source and the well plate cover 400. The angle of light 420 relative to base 401 is designed to ensure that light 420, to the extent that it is not refracted by well 404 and fluid 406, exits the bottom of well 404 in a direction orthogonal to the bottom of well 404. To this end, the angle of light 420 is set to account for both the refraction caused by sloped portion 412, and the refraction caused by base 401 (which is no longer orthogonal to light 420), e.g., based on the indices of refraction for the material (s) of well plate cover 400 and the environment, and in accordance with Snell's law. The incident angle(s) of light 402 may be set by inserting a special lens or other optical element(s), for example.

In an alternative embodiment, a collimated light source is used to provide light 420 at an angle orthogonal to the plane of base 401 (e.g., similar to light 320 of FIG. 3C), and the top side of base 401 (i.e., the side opposite the well 404) includes reciprocal graded surfaces to refract the light at the desired angle (e.g., rather than inserting a prism as described above). For example, the top side of base 401 may include, opposite each insertion element 402, a structure that mirrors sloped portion 412, but protrudes in the opposite (upward) direction. In this manner light entering and exiting well plate cover 400 may be collimated.

In any event, light 420 passes through the transparent insertion element 402 (or the transparent portion thereof) and, due to the lack of a meniscus and the angles of incidence for the incident light 420, there is relatively little noticeable refraction other than that which is caused by the contents of fluid 406 (i.e., the refraction needed to produce an accurate image of the fluid contents) and possibly portions of well 404. As seen in FIG. 4C, there may be a modest amount of fluid 406 that extends outside and above sloped portion 412 when insertion element 402 is fully inserted. In some embodiments where base 401 is also transparent, however, the entire well 404 and all of fluid 406 can nevertheless be imaged with insertion element 402 inserted. For example, some of light 420 may impinge upon the planar base 401 of well plate cover 400 in an orthogonal manner, allowing that light to pass around the perimeter of insertion element 402 without significantly refracting the light.

Figure 5A:
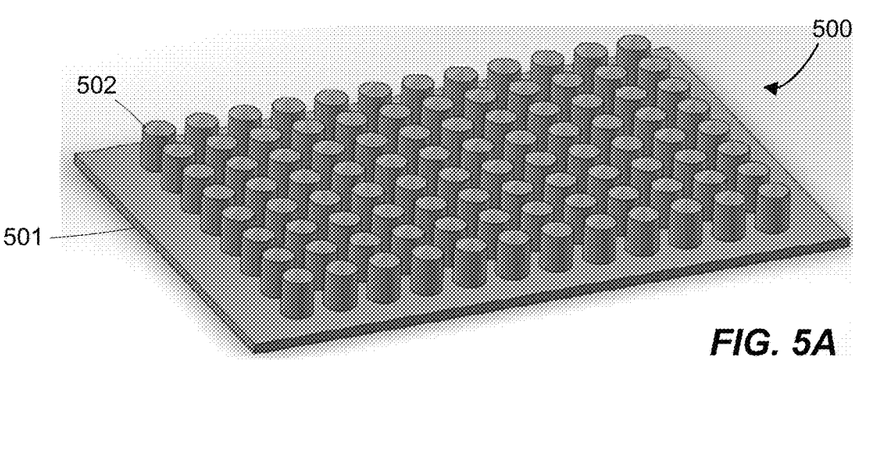
FIGS. 5A-5C depict a third embodiment of a well plate cover that may be used to resolve problems associated with the imaging of fluid samples in wells.
Figure 5B:
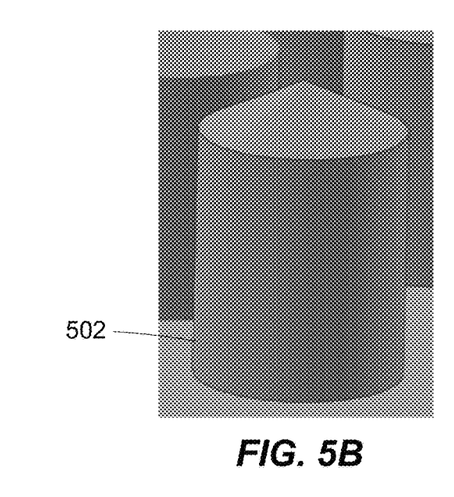
Figure 5C:
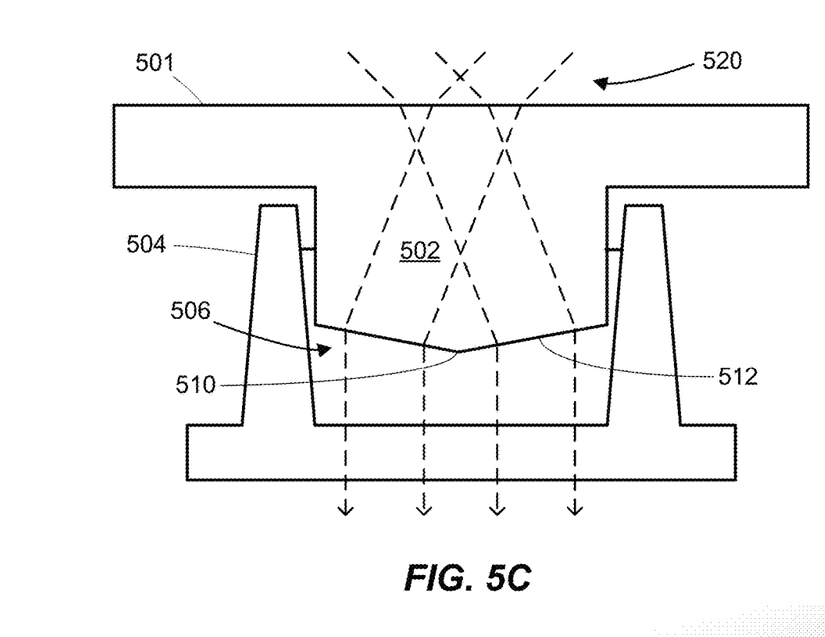

FIGS. 5A-5C depicts another alternative well plate cover 500 that may be used to resolve problems associated with the imaging of fluid samples in wells. Like well plate covers 300 and 400, well plate cover 500 may be used as a cover that fits to well plate 204, when imaging wells 206 with visual inspection system 200 of FIG. 2 as described above. Referring first to FIG. 5A, well plate cover 500 includes a planar base 501, from which protrude a number of insertion elements 502. In some embodiments, well plate cover 500 is a single, monolithic component. For example, the entire well plate cover 500 may be made of polystyrene, polypropylene, glass, or any other suitable transparent material. In other embodiments, insertion elements 502 are at least in part formed separately from (and/or of a different material than) base 501. In the example shown in FIG. 5A, well plate cover 500 provides 96 insertion elements 502 for a standard 96-well microplate. In other embodiments, however, well plate cover 500 may include more or fewer insertion elements 502, and/or may arrange insertion elements 502 in a different pattern on base 501. In still other embodiments, insertion elements 502 are not coupled to any base, and are inserted into wells (or other vessels) individually.

FIG. 5B provides a closer, 3D-perspective view of one of insertion elements 502, and FIG. 5C provides a cross-sectional view (not drawn to scale) of one of insertion elements 502. As seen in FIGS. 5B and 5C, each insertion element 502 has a distal end surface having/defining a conical shape. Referring specifically now to FIG. 5C, when insertion element 502 is being inserted into a well 504 containing a fluid 506 (e.g., into one of wells 206 of FIG. 2), an apex point 510 of insertion element 502 first contacts fluid 506. As insertion element 502 is inserted further into well 504, a sloped portion 512, which recedes from apex point 510 in all directions, then comes into contact with fluid 506. Insertion element 502 may be sized such that its maximum-diameter (cylindrical) portion can fit into well 504 with some tolerance, without allowing fluid 506 to form an appreciable meniscus outside the perimeter of insertion element 502. If well 504 has a base diameter of 6.35 mm and a top diameter of 6.86 mm, for example, insertion element 502 may have a diameter between 6.4 mm and 6.5 mm (to leave a small gap for air to escape). The total length of insertion element 502 may be set such that, when insertion element 502 is fully inserted into well 504, apex point 510 does not contact the bottom of well 504, but some, most or all of sloped portion 512 is submerged. For example, apex point 510 may be 6 mm away from base 501, in a direction orthogonal to base 501. The slope of sloped portion 412 may be such that air (or other gas) bubbles can quickly escape to the atmosphere. For example, sloped portion 512 may protrude 1 mm further into well 504 for every 3 mm traveled in a direction from the perimeter of insertion element 502 towards apex point 510 (or 0.5 mm further for every 3 mm, etc.). The appropriate length of insertion element 502 (i.e., the spacing between apex point 510 and base 501) may depend on the fluid fill volume. For lower fill volumes, for example, insertion element 502 may need to protrude further from base 501 to ensure that insertion element 502 fully engages/interacts with the fluid. While FIGS. 5A-5C depict an embodiment in which apex point 510 is centered within the distal end surface of insertion element 502, in other embodiments apex point 510 is not centered. For example, apex point 510 may be along the perimeter of sloped portion 512, in which case insertion element 502 is a cylinder terminated by an angled, flat plane (i.e., a plane that is neither orthogonal nor parallel to base 501 and the bottom of well 504).

Once insertion element 502 is fully inserted (e.g., with base 501 being some desired distance away from well 504, or in contact with well 504), fluid 506 may be imaged, with light 520 (e.g., sourced by illumination system 208 of FIG. 2) to provide illumination. As with insertion element 402 of FIG. 4C, however, light 520 may be provided at an angle to compensate for light refraction caused by sloped portion 512. If a collimated light source is used, for example, light 520 may be provided at the desired angle by inserting an axicon (conical prism) between the light source and the well plate cover 500. The angle of light 520 relative to base 501 is designed to ensure that light 520, to the extent that it is not refracted by well 504 and fluid 506, exits the bottom of well 504 in a direction orthogonal to the bottom of well 504. To this end, the angle of light 520 is set to account for both the refraction caused by sloped portion 512, and the refraction caused by base 501 (which is no longer orthogonal to light 520), e.g., based on the indices of refraction for the material(s) of well plate cover 500 and the environment, and in accordance with Snell's law. The incident angle of light 502 may be set by inserting a special lens or other optical element(s), for example.

In an alternative embodiment, a collimated light source is used to provide light 520 at an angle orthogonal to the plane of base 501 (e.g., similar to light 320 of FIG. 3C), and the top side of base 501 (i.e., the side opposite the well 504) includes a reciprocal, conical graded surface to refract the light at the desired angle (e.g., rather than inserting an axicon as described above). For example, the top side of base 501 may include, opposite each insertion element 502, a structure that mirrors sloped portion 512, but protrudes in the opposite (upward) direction. In this manner light entering and exiting well plate cover 500 may be collimated.

In any event, light 520 passes through the transparent insertion element 502 (or the transparent portion thereof) and, due to the lack of a meniscus and the angles of incidence for the incident light 520, there is relatively little noticeable refraction other than that which is caused by the contents of fluid 506 (i.e., the refraction needed to produce an accurate image of the fluid contents) and possibly portions of well 504. As seen in FIG. 5C, there may be a modest amount of fluid 506 that extends outside and above sloped portion 512 when insertion element 502 is fully inserted. In some embodiments where base 501 is also transparent, however, the entire well 504 and all of fluid 506 can nevertheless be imaged with insertion element 502 inserted. For example, some of light 520 may impinge upon the planar base 501 of well plate cover 500 in an orthogonal manner, allowing light to pass around the perimeter of insertion element 502 without significantly refracting the light.

Figure 6:
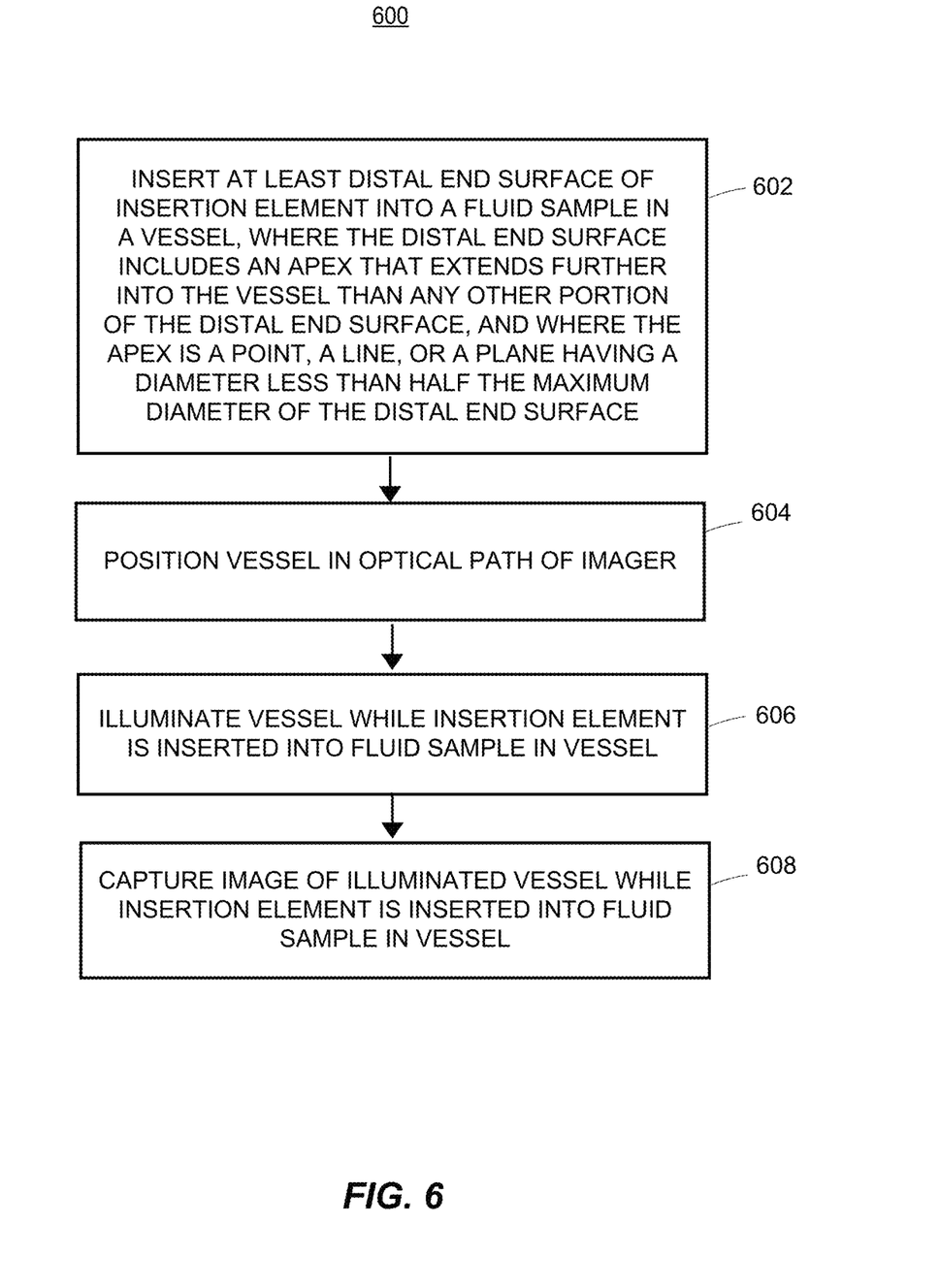
FIG. 6 is a flow diagram of an example method for imaging a fluid sample in a vessel.

It is understood that the examples of FIGS. 4-6 are merely illustrative, and that other embodiments that prevent or reduce the meniscus, while also reducing or eliminating air/gas bubbles, are also possible. For example, each insertion element may have a frustum shape (i.e., with a flat circular area at the tip of a truncated cone), and/or the edges of each insertion element (e.g., between an apex plane and another portion of the distal end surface) may be rounded or contoured, etc.

In some embodiments, at least a portion of each insertion element (e.g., insertion element 302, 402 or 502) is coated and/or treated to create a hydrophilic surface that faces/engages the fluid, which may facilitate the escape of air (or other gas) bubbles. For example, the insertion elements (or the entire cover, or just the insertion element surfaces that protrude the furthest from the cover base, etc.) may be subjected to a plasma treatment, or may be coated with a hydrophilic material, prior to use. By creating a hydrophilic surface on the insertion element, any bubble that does form may be forced to move until it escapes past the perimeter of the insertion element. In some applications (e.g., cell line monitoring), this may also have the advantage of preventing cell adhesion to the insertion element.

Additionally or alternatively, in some embodiments, the development of air bubbles may be mitigated using a flexible well plate cover. In such embodiments, the well plate cover may be slowly rolled onto the well plate, such that different insertion elements (or different rows of insertion elements, etc.) enter the wells at different times as the cover is rolled out. By causing each insertion element to enter its corresponding well at an angle (rather than coming down vertically into the well), air is less likely to become trapped beneath the insertion element. For example, the base/plane of the well plate cover (e.g., base 301, 401 or 501) may be formed from a flexible material (e.g., a thermoplastic elastomer (TPE) or other suitable material). In various embodiments, the insertion elements may be formed from the same flexible material as the rest of the cover (e.g., if that material is transparent), or from a different material (e.g., polystyrene, polypropylene or glass insertion elements that are inserted into/through an array of holes in a flexible sheet). A flexible well plate cover may be particularly advantageous for covers having relatively short insertion elements.

FIG. 6 is a flow diagram of an example method 600 for imaging a fluid sample in a vessel. Method 600 may be automatically implemented, in whole or in part, by one or more robotic systems (e.g., including visual inspection system 200 of FIG. 2), and/or may be performed in part by a human operator.

At block 602, at least a distal end surface of an insertion element is inserted into a fluid (e.g., liquid) sample in a vessel. The fluid sample may contain a medium that includes suitable nutrients for cells (e.g., amino acids, vitamins, etc.), growth factors, and/or other ingredients, for example, or may contain any other type of contents requiring inspection. The vessel may be a well in a well plate (e.g., well 206 in well plate 204), a syringe, a vial, or any other container that is susceptible to forming a meniscus when filled with a fluid. The insertion element may be one of multiple insertion elements protruding from a planar base, or may be a stand-alone insertion element.

At least a portion of the insertion element may be transparent and clear, to allow collimated light (e.g., when using a telecentric lens) to pass through the insertion element for imaging purposes. Alternatively, the insertion element may be made of diffuse material in order to provide omnidirectional lighting. The distal end surface of the insertion element includes an apex that, when the insertion element is properly inserted into the fluid sample in the vessel, extends further into the vessel than any other portion of the distal end surface. The apex may be a point or a line, for example. Alternatively, the apex may be a plane having a diameter substantially less than the maximum diameter of the distal end surface (i.e., when viewing the distal end surface from a perspective orthogonal to the direction of insertion). For example, an apex plane may be less than three-quarters, less than half, or less than one-quarter of the maximum diameter of the distal end surface. The insertion element may be similar to any insertion element described above in connection with FIGS. 4-6, for example. Block 602 may be performed by an automated/robotic system, for example, or may be performed by a human manually inserting the insertion element (e.g., by manually placing a well plate cover on a well plate).

At block 604, the vessel is positioned in an optical path of an imager (e.g., imager 212 of FIG. 2). Block 604 may be performed by an automated/robotic system (e.g., by visual inspection system 200 automatically moving stage 202), for example, or may be performed by a human manually positioning the vessel and/or the imager. In some embodiments where the distal end surface of the insertion element has a sloped portion, block 604 includes directing light so as to compensate for light refraction caused by the sloped portion (e.g., by a lens or other optical element(s) inserted in the optical path of the imager).

At block 606, the vessel is illuminated while the insertion element is inserted into the fluid sample. Block 606 may be performed by an automated/robotic system (e.g., by visual inspection system 200 automatically turning on a light source of illumination system 208), for example, or may in part be performed by a human who manually positions, and/or turns on, a light source. Block 606 may occur before block 602, between blocks 602 and 604, or after block 604.

At block 608, an image of the illuminated vessel is captured while the insertion element is inserted into the fluid sample. Block 608 may be performed by an automated/robotic system (e.g., by visual inspection system 200 automatically triggering imager 212), for example, or may in part be performed by a human manually positioning the vessel and/or triggering an imager. The captured image may then be stored in a memory and analyzed (e.g., by an automated inspection system, or by a human analyst).

Although the systems, methods, devices, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A well plate cover comprising:
   a base defining a base plane; and
   a plurality of insertion elements, wherein
   at least a portion of each of the insertion elements is transparent,
   each of the insertion elements (i) is coupled to the base, and (iii) extends, in a direction orthogonal to the base plane, from the base to a distal end surface of the insertion element,
   the distal end surface of each of the insertion elements includes an apex that, when the respective insertion element is inserted into a well of a well plate, extends further into the well than any other portion of the distal end surface, and
   the apex is an apex plane having a diameter that is less than one half of a maximum diameter of the distal end surface;
   the apex plane of each of the distal end surfaces forms a circle; and
   the distal end surface of each of the insertion elements includes a plurality of planar tiers that (i) form concentric rings around the respective apex plane and (ii) are sized to extend into the well, with each successive planar tier, when progressing outwardly from the apex plane towards a perimeter of the distal end surface, is closer to the base than is the previous planar tier.

2. The well plate cover of claim 1, wherein at least a portion of each insertion element is coated and/or treated with a hydrophilic surface.

3. A method for imaging a fluid sample in a vessel, the method comprising:
   inserting at least a distal end surface of an insertion element into the fluid sample in the vessel,
   wherein at least a portion of the insertion element is transparent,
   wherein the distal end surface includes an apex that extends further into the vessel than any other portion of the distal end surface, and
   wherein the apex is an apex plane having a diameter that is less than one half of a maximum diameter of the distal end surface; wherein:
   the apex plane forms a circle;
   the insertion element includes a proximal end opposite the distal end surface;
   the distal end surface includes a plurality of planar tiers that (i) form concentric rings around the apex plane and (ii) are sized to extend into the well; and
   each successive planar tier, when progressing outwardly from the apex plane towards a perimeter of the distal end surface, is closer to the proximal end of the insertion element than is the previous planar tier;
   positioning the vessel in an optical path of an imager;
   illuminating the vessel while the insertion element is inserted into the fluid sample in the vessel; and
   capturing, by the imager, an image of the illuminated vessel while the insertion element is inserted into the fluid sample in the vessel.

4. The method of claim 3, wherein at least a portion of each insertion element is coated and/or treated with a hydrophilic surface.

* * * * *